United States Patent [19]

Bryant

[11] 4,143,075

[45] Mar. 6, 1979

[54] CONTROL OF CONDENSATION PRODUCTS IN HYDROFORMYLATION PROCESS

[75] Inventor: David R. Bryant, South Charleston, W. Va.

[73] Assignee: Union Carbide Corporation, New York, N.Y.

[21] Appl. No.: 713,680

[22] Filed: Aug. 12, 1976

[51] Int. Cl.² .......................................... C07C 45/02
[52] U.S. Cl. .............................................. 260/604 HF
[58] Field of Search ................. 260/604 HF, 632 HF, 260/429 J; 568/909

[56] References Cited

U.S. PATENT DOCUMENTS

| 3,239,566 | 3/1966 | Slaugh ........................... 260/604 HF |
| 3,253,018 | 5/1966 | Zachry et al. .................. 260/632 HF |
| 3,527,809 | 9/1970 | Pruett et al. ................... 260/604 HF |
| 3,576,881 | 4/1971 | Senn ................................ 260/483 |
| 3,647,845 | 3/1972 | Wilkes ............................ 260/439 R |

FOREIGN PATENT DOCUMENTS

| 903589 | 8/1962 | United Kingdom ............ 260/604 HF |
| 1228201 | 4/1971 | United Kingdom ............ 260/604HF |
| 1338237 | 11/1973 | United Kingdom ............ 260/604 HF |
| 1387657 | 3/1975 | United Kingdom ............ 260/604 HF |

OTHER PUBLICATIONS

Harris, J. Amer. Ceramic Society, vol. 56, No. 4 (1973).
Brief et al, Amer. Ind. Hyg. Ass. S U(1) (1967).

Primary Examiner—James O. Thomas, Jr.
Assistant Examiner—Werren B. Lone
Attorney, Agent, or Firm—Bernard Lieberman

[57] ABSTRACT

Hydroformylating alpha-olefins in a cyclic homogeneous liquid phase process utilizing a modified rhodium catalyst in which iron is introduced into the reaction as a contaminant thereof, the improvement which comprises controlling the degree of condensation of aldehyde within the homogeneous liquid phase process by controlling the amount of iron which is provided within the homogeneous liquid phase.

10 Claims, 3 Drawing Figures

EFFECT OF IRON COMPOUNDS ON BUTYRALDEHYDE TRIMERIZATION

FIG. 1

EFFECT OF IRON COMPOUNDS ON BUTYRALDEHYDE TRIMERIZATION

- 300 ppm Fe as Iron Octanoate and 500 ppm Rhodium
- 300 ppm Fe as Iron Pentacarbonyl and 500 ppm Rhodium
- Control – No iron or rhodium

CONTROL OF CONDENSATION PRODUCTS IN HYDROFORMYLATION PROCESS

This invention relates to the preparation of aldehydes by the hydroformylation process in which an alpha-olefin is hydroformylated with carbon monoxide and hydrogen in the presence of a rhodium catalyst. This process is directed to controlling the self-condensation of aldehyde as produced by the hydroformylation process by controlling the amount of iron which is present in the reaction.

In copending application, Ser. No. 674,823, filed Apr. 18, 1976, there is described a cyclic process for effecting hydroformylation which involves establishing a liquid body of a homogeneous mixture containing the olefin, carbon monoxide and hydrogen being supplied thereto, aldehyde products and higher boiling aldehyde condensation products being continuously formed therein, a soluble rhodium catalyst complexed with carbon monoxide and a triaryl phosphine. At least ten moles of triaryl phosphine are provided to the liquid body for each mole of rhodium metal. A gaseous recycle stream is supplied to the liquid body comprising hydrogen and olefin with make-up quantities of carbon monoxide, hydrogen and olefin being also supplied to the liquid body. The temperature of the liquid body is maintained at about 50 degrees C. to about 130 degrees C., and the total pressure is maintained at less than about 400 pounds per square inch absolute. The carbon monoxide partial pressure in the reaction is less than about 50 pounds per square inch absolute and the hydrogen partial pressure is less than about 200 pounds per square inch absolute. There is removed from the liquid body a vaporous mixture comprising olefin, hydrogen, vaporized aldehyde products and an amount of vaporized aldehyde condensation products essentially equal to the rate of their formation in the body whereby the size of the liquid body is maintained at a predetermined value. Aldehyde products and aldehyde condensation products are recovered from the vaporous mixture and this forms the gaseous recycle stream which is supplied to the liquid body as mentioned above.

U.S. Pat. No. 3,527,809, entitled "Hydroformylation Process" by R. L. Pruett and J. A. Smith, issued Sept. 8, 1970, discloses a significant development in hydroformylation of alpha-olefins to produce aldehydes at high yields, low temperatures and pressures, with excellent catalyst stability, the product aldehyde mixtures containing a high normal to iso- (or branched-chain) isomer ratio. The process employs certain rhodium complex compounds to effectively catalyze under a defined set of variables, in the presence of select triorgano phosphorus ligands, the hydroformylation of olefins with hydrogen and carbon monoxide. The variables include (1) the rhodium complex catalyst, (2) the olefin feed, (3) the triorgano phosphorus ligand and its concentration, (4) a relatively low temperature range, (5) a relatively low total hydrogen and carbon monoxide pressure, and (6) a limitation on the partial pressure exerted by carbon monoxide. The process of this invention adopts the variables of the invention of the aforementioned U.S. Patent Application and the aforementioned Pruett et al. patent.

One problem associated with the process set forth in the aforementioned Ser. No. 674,823 is the necessity to control the size of the liquid body and at the same time effectively produce a desired amount of the aldehyde products. As pointed out in the body of that application and as set forth in copending U.S. Patent Application, Ser. No. 683,534, filed May 5, 1976, a continuation of Ser. No. 556,270, filed Mar. 7, 1975, which, in turn, is a continuation of Ser. No. 887,370, filed Dec. 22, 1969, from which British Patent Specification No. 1,338,237 is derived, aldehyde products formed in the liquid body self-condense to produce a higher molecular weight condensation product which has been determined to be an extremely good solvent for the catalyst of this hydroformylation process. Said British Specification also discloses a liquid recycle process in which the catalyst containing the higher molecular weight condensation products and the aldehyde products is continuously or intermittently fed from the reactor to a distillation zone (or aldehyde recovery zone) where the aldehyde product is recovered along with unreacted gaseous products. The liquid body in the recovery zone is then recycled to the reactor. In so doing, the catalyst is not required to undergo a separation from the liquid body comprising the reaction medium. In this process purge streams which undergo separate treatments are the mechanism for controlling the build-up of the condensation products. However, if the hydroformylation processes disclosed in Ser. No. 674,823 and British Patent Specification No. 1,338,237 result in excessive amounts of condensation products being formed during the hydroformylation reaction then, of course, a substantial portion of the aldehyde product has been converted into a less desirable condensation product whose main function in the process is as a catalyst solvent and not as a saleable product. It is therefore desirable to allow the reaction to produce only a certain minimum amount of condensation products, at least in the initial stages of the reaction if that is sought, or to produce the condensation products separately and introduce them into the reaction after which additional condensation product formation can be minimized in favor of production of the desired aldehyde products.

It has been determined over constant practice of the process described in Ser. No. 674,823 and said British Patent Specification that the concentration of the condensation products in the liquid body can be controlled to an extent which allows for continuous effective operation of the process, by controlling the iron content in the liquid body. This invention recognizes the significant fact that iron in the liquid body will act to convert aldehyde products to condensation products at a faster rate than aldehyde will self-condense in the absence of the iron. Specifically, iron salts convert aldehydes to their corresponding dimers and trimers and lower unit productivity by dilution of the rhodium catalyst. The iron content is kept at a level correlated with the rate of formation of the condensation products such that the amount of condensation products formed does not exceed the total amount of condensation products which is sought in the liquid body plus that which is removed from the liquid body either with the vaporous mixture (when practicing the process of Ser. No. 674,823) or the purge stream (when practicing the process of said British Patent).

U.S. Pat. No. 3,253,018 states at column 4, lines 41–47 that iron is a catalyst poison, particularly "iron carbonyl". The patent states "the removal of such poisons is readily accomplished by passing the stream under pressure through a bed of solid absorbent, e.g., molecular sieve, prior to use in the present process". The process of that patent is concerned with catalyst poisoning by iron carbonyl which is not a problem in the practice of the process of Ser. No. 674,823. Iron carbonyl, better characterized as iron pentacarbonyl, at concentrations typically found in the reaction medium is not detrimental to the Rh catalyst described in Ser. No. 674,823. It is believed that when the $Fe(CO)_5$ is converted to an iron salt, the formed ionic iron becomes a condensation catalyst for the aldehyde products produced in the process of Ser. No. 674,823. Moreover, U.S. Pat. No. 3,253,018 describes a batch process in which aldehyde condensation could not prove to be a problem because before any significant amount of condensation products could be produced, the reaction is stopped and the products separated. In the cobalt catalyzed Oxo reactions, as pointed out in Ser. No. 674,823, the catalyst is continuously removed from the reactor in the same manner as the products of the reaction. In so doing, the aldehyde product is recovered from an environment in which its condensation could develop. That is, cobalt catalyzed Oxo reactions are characterized by low catalyst residence time, hence there is little opportunity for iron to catalyze aldehyde condensation. It has been determined that a small amount of $Fe(CO)_5$ in the Cobalt Oxo reactor is not enough to provide the basis for subsequent formation of the ionic iron which catalyzes the aldehyde condensation reaction. Thus, the problem associated with $Fe(CO)_5$ in rhodium catalyzed Oxo processes inherently did not exist in the Co catalyzed Oxo art.

SUMMARY OF THE INVENTION

This invention describes a process for controlling the concentration of aldehyde condensation products formed during the rhodium catalyzed hydroformylation of an alpha-olefin containing two to about twenty carbon atoms as practiced pursuant to the gas and liquid recycle inventions described in the aforementioned copending applications and British Patent Specification. The process of the invention comprises feeding the alpha-olefin together with hydrogen and carbon monoxide at a prescribed temperature and pressure through a reaction zone containing the catalyst dissolved in the liquid body, the catalyst being essentially non-volatile and being effective for hydroformylation of the alpha-olefin. Iron salt contaminants which serve to promote the self-condensation of aldehyde are continuously formed in the liquid body. The level of aldehyde condensation product in the liquid body is controlled by selectively removing iron salt contaminants from said liquid body without removing rhodium catalyst in an amount sufficient to maintain the formation of condensation product at or below a preselected value.

Iron removal from rhodium catalyst Oxo solutions is preferably effected with the use of sequestering agents which remove ionic iron from solution but not the rhodium catalyst. Sequestering agents belong to the general class called chelates, which in turn belong to the larger group called ligands, the latter being materials which coordinate with metal ions. Chelates are multifunctional ligands having two or more sites for coordination with metal ions. A sequestering agent is a material which forms a water-soluble chelate complex of a metal. Ethylene diaminetetraacetic acid (EDTA) and similar aminopolycarboxylic acids are preferred sequestering agents for purposes of the present invention.

The principal chelate donating groups include:

| Group | Name |
|---|---|
| $-NH_2$ | Primary amino |
| $-NH$ | Secondary amino |
| $-N$ | Tertiary amino |
| $-C=NOH$ | Oxime |
| $-C=NH$ | Imino |
| $-C=NR_3$ | Substituted imino |
| $-S-$ | Thioether |
| $-C=O$ | Keto |
| $-C=S$ | Thio Keto |
| $-O^-$ | Hydroxyl |
| $-S^-$ | Thioalcohol |
| $-COO^-$ | Carboxylate |
| $-\overset{O}{\underset{OH}{\overset{\|}{P}}}-O^-$ | Phosphonate |
| $-\overset{O}{\underset{O}{\overset{\|}{S}}}-O^-$ | Sulfonate |

The above-described chelate donating groups can be combined in numerous ways to define a wide variety of chelating agents. The broad classifications of such chelating agents include the following: aliphatic carboxylic acids such as, oxalic acid; aromatic carboxylic acids such as 5-sulfosalicylic acid; aliphatic amines such as, triaminotriethylamine; aromatic amines such as, o-phenanthroline; simple amino aliphatic hydroxy acids such as tartaric acid; aromatic hydroxy acids such as, 5-sulfosalicylic acid; hydroxy aldehydes such as, salicylaldehyde; beta-diketones such as, acetylacetone; phenolic compounds such as, pyrocatechol disulfonic acid; condensed phosphates such as, sodium pyrophosphate, sodium tripolyphosphate, sodium tetrapolyphosphate and sodium polyphosphate; and aminopolycarboxylic acids such as, ethylenediamine tetraacetic acid.

Removal of iron from the rhodium solution may also be carried out by circulating the liquid Oxo solution through a macroreticular ion exchange membrane, or by precipitating the iron out of the catalyst solution in a sidestream with materials such as sulfides.

DETAILED DESCRIPTION OF THE INVENTION

The hydroformylation process of the invention contemplates the use of alpha-olefins of 2 to 20 carbon atoms, preferably 2 to 10 carbon atoms. Such alpha-olefins are characterized by a terminal ethylenic carbon-to-carbon bond which may be a vinylidene group, i.e., $CH_2=C<$, or a vinyl group, i.e., $CH_2=CH-$. They may be straight-chain or branched-chain and may contain groups or substituents which do not essentially interfere with the course of this process. Illustrative alpha-olefins include ethylene, propylene, 1-butene, iso-butylene, 2-methyl-1-butene, 1-pentene, 1-hexene, 1-heptene, 1-octene, 1-dodecene, 1-octadecene, and the like.

The reaction is advantageously conducted at a temperature of from about 50° C. to about 130° C. A temperature in the range of from about 60° C. to about 120° C. is preferred and it will usually be convenient to operate at a temperature of from about 90° to about 115° C.

Total pressures less than about 400 psia and as low as one atmosphere, and lower, can be employed with effective results. Total pressures of less than 350 psia are preferred. In general, a partial pressure attributable to hydrogen of from 25 to 95 percent and more, based on the total gas pressure (CO + $H_2$) is suitable. It is generally advantageous to employ a total gas pressure in which the partial pressure attributable to hydrogen is greater than the partial pressure attributable to carbon monoxide, e.g., the hydrogen to carbon monoxide ratio being between 3:2 and 20:1.

The partial pressure of the alpha-olefin in the reaction zone may be up to about 35 percent of the total pressure, preferably in the region of 10 to 20 percent of the total pressure.

In a preferred operation the CO partial pressure is typically not in excess of about 50 psia, most desirably not in excess of about 35 psia. The preferred hydrogen partial pressure should be less than about 200 psia.

The catalyst may be any non-volatile catalyst that is effective for hydroformylation of alpha-olefins but in view of the known advantages as taught in U.S. Pat. No. 3,527,809 of catalysts based on rhodium, it constitutes in modified form the catalyst of choice. When a $C_3$ or higher olefin is used as a starting material it is preferred to choose a catalyst that gives a high n-/iso-ratio in the aldehyde product mixture. The general class of rhodium catalysts depicted in U.S. Pat. No. 3,527,809 may be used in the practice of this invention.

The preferred catalyst of this invention comprises rhodium complexed with carbon monoxide and a triarylphosphine ligand. The most desirable catalyst is free of halogen such as chlorine, and contains hydrogen, carbon monoxide and triarylphosphine complexed with rhodium metal to produce a catalyst soluble in the aforementioned liquid body and stable under the conditions of the reaction. Illustrative triarylphosphine ligands are triphenylphosphine, trinaphthylphosphine, tritolyphosphine, tri(p-biphenyl)phosphine, tri(p-methoxyphenyl)phosphine, tri(m-chlorophenyl)phosphine, p-N,N-dimethylaminophenyl bis-phenyl phosphine, and the like.

Rhodium is preferably introduced into the liquid body as a preformed catalyst, e.g., a stable crystalline solid, rhodium hydridocarbonyl-tris(triphenylphosphine), $RhH(CO)(PPh_3)_3$. The rhodium can be introduced to the liquid body as a precursor form which is converted in situ into the catalyst. Examples of such precursor form are rhodium carbonyl triphenylphosphine acetylacetonate, $Rh_2O_3$, $Rh_4(CO)_{12}$, $Rh_6(CO)_{16}$, and rhodium dicarbonyl acetylacetonate. Both the catalyst compounds which will provide active species in the reaction medium and their preparation are known by the art, see Brown et al., *Journal of the Chemical Society*, 1970, pp. 2753-2764.

In ultimate terms the rhodium concentration in the liquid body can range from about 25 ppm to about 1200 ppm of rhodium calculated as free metal, and the triarylphosphine is present in the range of about 0.5 percent to about 30 percent by weight, based on the weight of the total reaction mixture, and in an amount sufficient to provide at least 10 moles of free triarylphosphine per mole of rhodium.

It is preferred to effect the process of the invention using a liquid phase in the reaction zone which contains one of the aforementioned rhodium complex catalysts and, as a solvent therefor, higher boiling liquid aldehyde condensation products (as hereinafter defined) which are rich in hydroxylic compounds.

By the term "higher boiling liquid aldehyde condensation products" as used herein is meant the complex mixture of high boiling liquid products which result from the condensation reactions of the $C_3$ to $C_{21}$ alkanal product of the process of the invention, as illustrated below in the series of equations involving n-butyraldehyde as the model. Such condensation products can be preformed or produced in situ in the Oxo process. The rhodium complex species is soluble in these relatively high boiling liquid aldehyde condensation products while exhibiting high catalyst life over extended periods of continuous hydroformylation.

Initially, the hydroformylation reaction can be effected in the absence or in the presence of small amounts of higher boiling liquid aldehyde condensation products as a solvent for the rhodium complex, or the reaction can be conducted with up to about 70 weight percent, and even as much as about 90 weight percent, and more, of such condensation products, based on the weight of the liquid body. A small amount of the higher boiling liquid aldehyde condensation products can be as little as 5 weight percent, preferably more than 15 weight percent, based on the weight of the liquid body.

The condensation products of the aldehydes are aldol condensation products varying in molecular weight ranging from dimer structures to tetramer structures and greater in terms of molecular weight. To illustrate the kind of condensation products that are feasible from the aldol condensation of butyraldehyde, reference is made to the following discussion:

In the hydroformylation of, for example, propylene, two products are possible, namely normal and iso-butyraldehydes. Since normal butyraldehyde is the more attractive product commercially, high normal/iso ratios of butyraldehydes are desirable. However, the aldehydic products being reactive compounds themselves slowly undergo condensation reactions, even in the absence of catalysts and at comparatively low temperatures, to form high boiling liquid condensation products. Some aldehyde product, therefore, is involved in various reactions as depicted below using n-butyraldehyde as an illustration:

In addition, aldol I can undergo the following reaction:

(tetramer VII)

The names in parentheses in the aforeillustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self condensation of iso-butyraldehyde and a further range of compounds is formed by condensation of one molecule of normal butyraldehyde with one molecule of iso-butyraldehyde. Since a molecule of normal butyraldehyde can aldolize by reaction with a molecule of iso-butyraldehyde in two different ways to form two different aldols VIII and IX, a total of four possible aldols can be produced by condensation reactions of a normal/iso mixture of butyraldehydes.

Aldol I can undergo further condensation with isobutyraldehyde to form a trimer isomeric with trimer III and aldols VIII and IX and the corresponding aldol X produced by self condensation of two molecules of isobutyraldehyde can undergo further reactions with either normal or isobutyraldehyde to form corresponding isomeric trimers. These trimers can react further analogously to trimer III so that a complex mixture of condensation products is formed.

It is highly desirable to maintain the substituted acrolein II and its isomers at low concentrations, e.g. below about 5 weight percent. The substituted acrolein II, specifically termed 2-ethyl-3-propylacrolein ("EPA"), is formed in situ along with other condensation products and has been found to inhibit catalyst activity. The ultimate effect of EPA or like products is to reduce hydroformylation rates to such an extent that any process where the EPA is present in amounts greater than about 5 weight percent, even greater than about one percent by weight based on the weight of the liquid body, will suffer an economic penalty. However, when the alpha-olefin is ethylene, this type of acrolein derivative is not found to adversely affect the catalytic reaction and, therefore, its buildup in the reaction medium is not a critical issue.

The conversion of aldehydes to their corresponding dimers and trimers is believed to be catalyzed primarily by iron salt in the rhodium Oxo solution and, to a far lesser extent by zero valent non-ionic complexes of iron, such as, iron pentacarbonyl. Initially, iron pentacarbonyl is formed when carbon monoxide in the synthesis gas contacts an iron-containing surface. Under non-equilibrium conditions, the level of iron pentacarbonyl in the gas stream depends on the state of the metal surface, contact time, temperature and gas partial pressure. Iron pentacarbonyl reacts with the ligand used to moderate the oxo reaction to produce a complex (i.e., a zero valent ligand substituted metal carbonyl) with low volatility which remains in the catalyst solution where it can undergo further reaction. Traces of oxygen convert such complex to divalent or trivalent iron.

Figure 1:
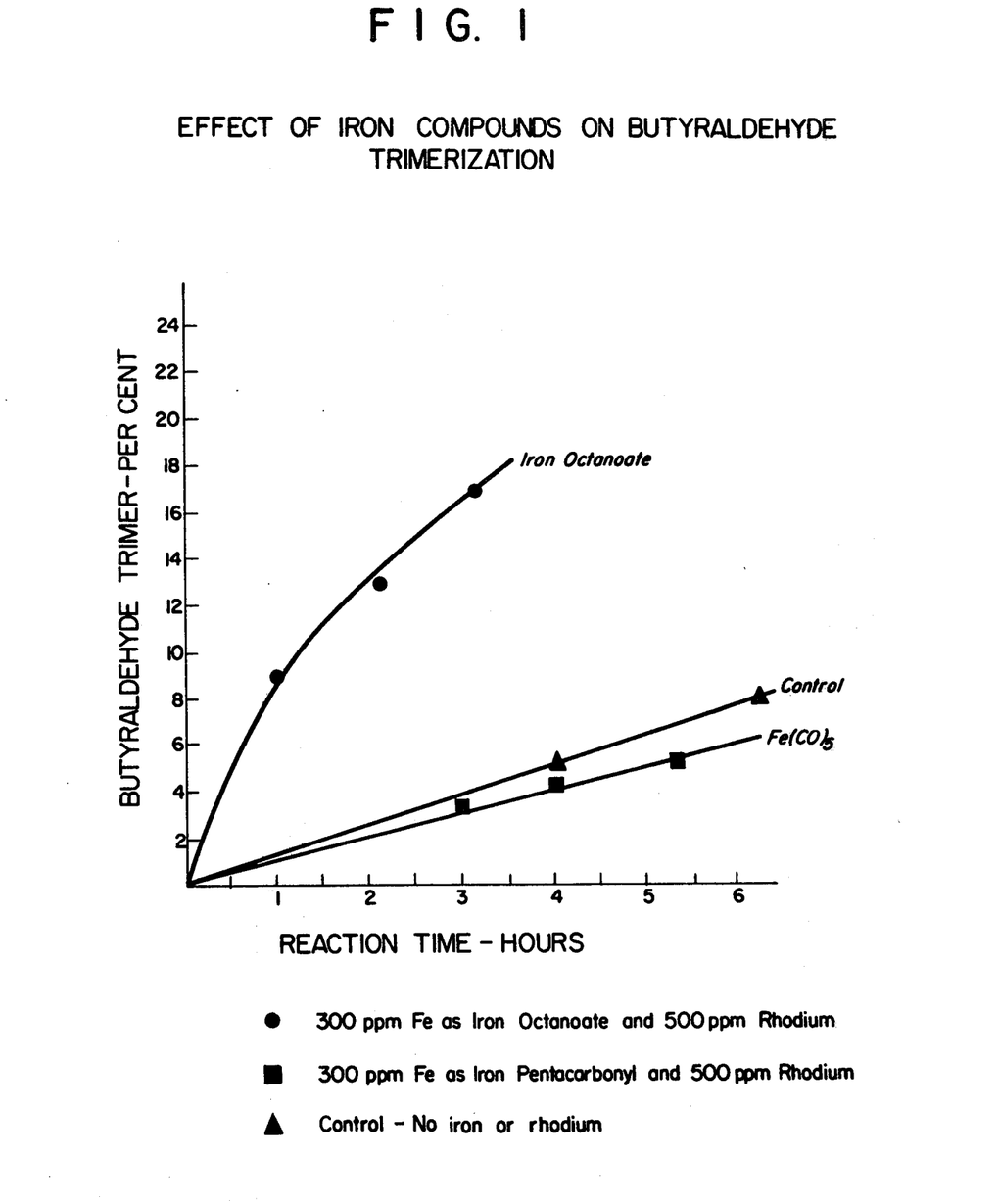
FIG. 1 is a graph illustrating the effect of ionic and non-ionic iron on trimerization of butyraldehyde.

Reference to FIG. 1 shows the effect of iron compounds on the trimerization of butyraldehyde. Trimer concentration is plotted as a function of time for samples of Oxo catalyst solution containing 500 ppm rhodium in combination with ionic iron (iron octanoate) and with a non-ionic complex of iron (iron pentacarbonyl). A control sample containing no iron or rhodium was also tested. Test conditions were a temperature of 130° C. and 100 psig partial pressure each of carbon monoxide and hydrogen. The sample containing iron pentacarbonyl affected the reaction essentially the same as the control sample. The presence of ionic iron in rhodium Oxo solution is seen to have a significant effect on trimerization of butyraldehyde.

In actual practice, the presence of a preselected concentration of trimer in the catalyst solution is desirable. For purposes of start-up, the present invention contemplates the addition of iron salts to catalyze aldehyde condensation so as to reach a steady state operating condition more quickly. Thereafter iron salts are removed from solution to maintain the level of aldehyde condensation products at the desired value.

Iron removal from the Oxo catalyst solution is preferably carried out using a water-soluble chelating agent to form a water-soluble iron complex. The catalyst solution may be contacted with the chelating agent batchwise, or by means of a continuous side stream from the reactor. An additional organic component such as cyclohexanone or a product aldehyde may be added to the organic phase to promote separation of the organic and aqueous layers.

The concentration of sequestering agent in the aqueous fraction used for extraction is not critical. For total complexation of iron, one or more moles of sequestering agent per mole of iron are required. If less than this ratio is used, only a fraction of the iron is removed.

The pH of the aqueous solution can vary over a wide range without adversely affecting iron extraction. Since highly acidic or basic conditions enhance condensation of aldehydes it may be beneficial in certain instances to adjust the solution pH to a range of from about 3.5 to 10.

Sodium salts of ethylenediamine tetraacetic acid ("EDTA") and related aminopolycarboxylic acids such as disodiumnitrilotriacetate are among the most useful sequestering agents for purposes of the present invention. Other ligands which are reported in the literature to complex with both divalent and trivalent iron (see Bjerrum et al., "Stability Constants of Metal-Iron Complexes, with Solubility Products of Inorganic Substances", London, the Chemical Society, 1967; and Martell and Calvin, "Chemistry of the Metal Chelate Compounds", New York, Prentice-Hall Inc., 1952, Appendix I) and are useful for the present invention include: oxalic acid; malonic acid; cystene (2-amine-B-mercaptopropionic acid); tartaric acid; acetylacetone; citric acid; gluconic acid; nitrilotriacetic acid; N-2-hydroxyethyliminodiacetic acid; ethylenediamine-N,N-diacetic acid; 2'-hydroxy-pyridino(3':4'-2:3)pyrazine; 8-hydroxycinnoline; 8-hydroxyl-1,7-naphthyridine; ethylenediamine-N,N'-dipropionic acid; 8-hydroxyquinoline; 8-hydroxyquinoline-5-sulfonic acid; 2-hydroxycyclohexyliminodiacetic acid; 2,6-di(2-pyridyl)pyridine; ethylenediamine; diethylenetriamine; triethylenetetramine; B,B',B"-triaminotriethylamine; bipyridyl; 1,10-phenanthroline; 5-chloro-1,10-phenanthroline; 5-nitro-1,10-phenanthroline; 5-methyl-1,10-phenanthroline; 5-phenyl-1,10-phenanthroline; alanine; asparagine; glycine; methionine; phenylalanine; serine; tryptophan; valine; ethylenediamine tetrapropionic acid; salicylic acid; 5-sulfosalicylic acid; salicylaldehyde; benzoylacetone; benzoyltrifluoroacetone; dibenzoylmethane; 2-furoyl-benzoylmethane; 3,6-disulfo-1,8-dihydroxynaphthalene(chromotropic acid); 3,5-disulfopyrocatechol; 1,2-diaminocyclohexane, N,N,N'-tetracetic acid; versene Fe-3(tradename); methylaminediacetic acid; diethylenetriaminepentaacetic acid; ethylene glycol-bis-(B-aminoethylether)-N,N'-tetraacetic acid; ethyletherdiaminetetraacetic acid; N-hydroxyethylenediaminetriacetic acid; 1-methylethylenediaminetetraacetic acid (or 1,2-propylenediaminetetraacetic acid); N,N-dihydroxyethylglycine; ethylenediamine N,N,N',N-tetrapropionic acid. For many of the above-described ligands, shown in protonated form, the alkali metal salts are preferred for purposes of the invention.

Figure 2:
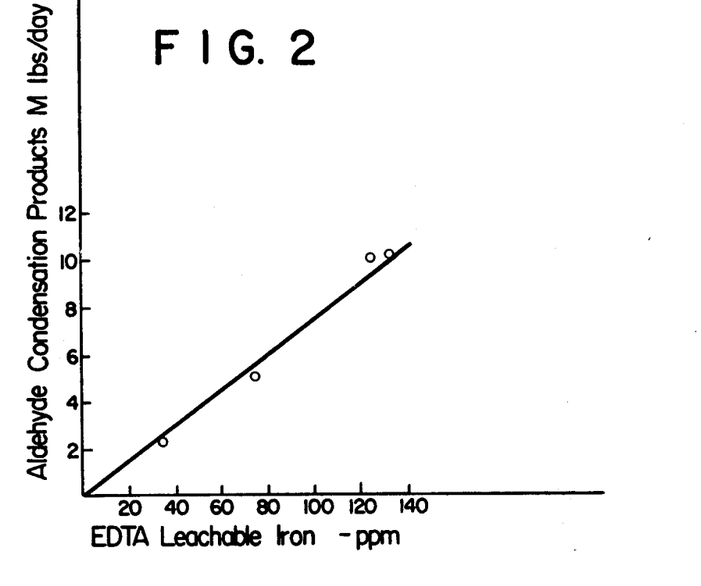
FIG. 2 is a plot of aldehyde condensation products as a function of leachable iron concentration in the catalyst solution.

With reference to FIG. 2, the production rate of aldehyde condensation products in a rhodium catalyzed hydroformylation process is shown plotted as a function of the iron salt concentration in the catalyst solution. More specifically, the graph reflects data from an operating Oxo plant wherein samples of catalyst solution were periodically withdrawn and the iron content extracted with an excess of disodio EDTA in a 0.5 (wt.) percent aqueous solution. The concentration of iron in the organic phase of the solution was measured before and after the extraction step, the difference representing "EDTA leachable iron". As seen from the graph, the production rate of condensation products varies linearly with the quantity of leachable iron in the catalyst solution.

The invention is further illustrated with reference to FIG. 3, which schematically shows a diagrammatic flowsheet suitable in practising the process of the invention.

Figure 3:
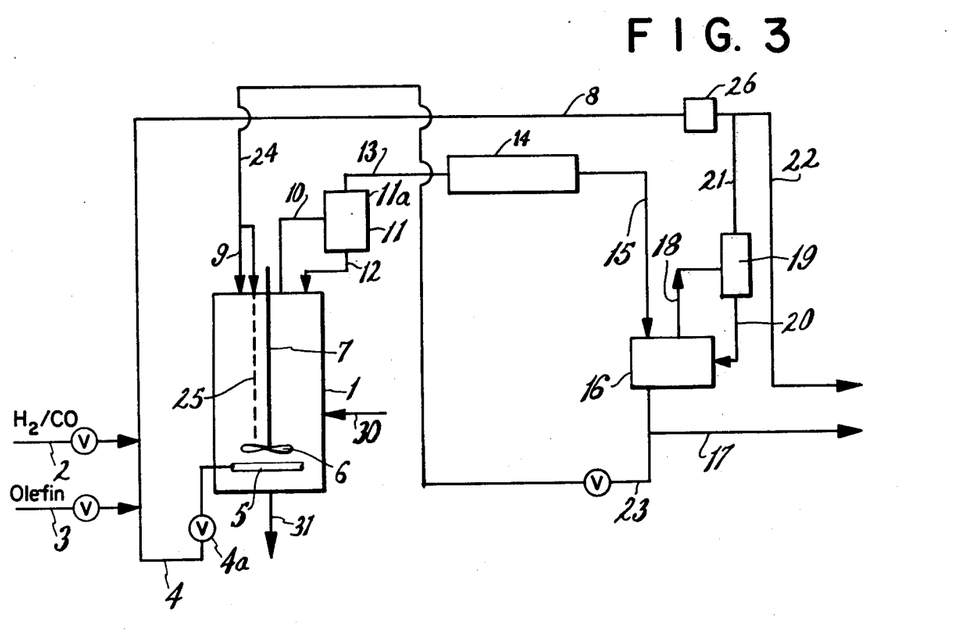
FIG. 3 is a schematic drawing of a flow sheet representing one embodiment of the process of the invention wherein product removal is effected with a gas recycle stream.

Referring to FIG. 3, a stainless steel reactor 1 is provided with one or more disc impeller 6 containing perpendicularly mounted blades and rotated by means of shaft 7, by a suitable motor (not shown). Located below the impeller 6 is a circular tubular sparger 5 for feeding the α-olefin, and synthesis gas plus the recycle gas. The sparger 5 contains a plurality of holes of sufficient size to provide sufficient gas flow into the liquid body at about the impeller 6 to provide the desired amount of the reactants in the liquid body. The reactor is also provided with a steam jacket (not shown) by means of which the contents of the vessel can be brought up to reaction temperature at start-up and internal cooling coils (not shown).

Vaporous product effluent from the reactor 1 are removed via line 10 to separator 11 where they are passed through a demisting pad 11a therein to return some aldehyde and condensation product and to prevent potential carry-over of catalyst. The reactor effluent is passed by line 13 to a condenser 14 and then through line 15 to catchpot 16 in which the aldehyde product and any by-product can be condensed out of the off gases (effluent). Condensed aldehyde and by-products are removed from the catchpot 16 by line 17. Gaseous materials are passed via line 18 to separator 19 containing a demisting pad and recycle line 20. Recycle gases are removed by line 21 to line 8 from which a purge through line 22 is pulled to control saturated hydrocarbon content. The remaining and major proportion of the gases can be recycled via line 8 to line 4 into which is fed make-up reactant feeds through lines 2 and 3. The combined total of reactants are fed to the reactor 1. Compressor 26 aids in transporting the recycle gases.

Iron salts may be conveniently removed from the catalyst solution in reactor 1 in a batchwise manner by periodically introducing sequestering agent into the reactor through inlet line 30. After suitable agitation of the catalyst solution with impeller 6, the catalyst solution is allowed to separate into an iron-containing aqueous phase and an organic phase, the bottom layer aqueous phase being thereafter removed from the catalyst solution via line 31.

Alternatively, the catalyst solution may be treated outside of the reactor 1 in a sidestream (not shown) to remove iron salt from the catalyst solution. Thus, for example, iron may be removed from solution by ion exchange with a macroreticular exchange membrane. Similarly, iron may be precipitated from solution with sulfides, the remaining solution being thereafter recirculated to the reactor 1. It should be noted, however, that the use of a precipitant may adversely affect the rhodium catalyst necessitating further treatment or purification of the catalyst prior to its use in the reaction.

Fresh catalyst solution can be added to the reactor 1 by line 9. The single reactor 1 can of course, be replaced by a plurality of reactors in parallel.

The crude aldehyde product of line 17 can be treated by conventional distillation to separate the various aldehydes and the condensation products. A portion of the crude can be recycled to reactor 1 through line 23 and fed as indicated by broken-line 25 to a point above impeller 6 for the purpose of maintaining the liquid level in reactor 1 if such is required.

EXAMPLE 1

A variety of sequestering and chelating agents were tested using a prepared stock solution containing 300 ppm iron as iron naphthenate in Texanol solvent. An equal weight of cyclohexanone was added to facilitate water-organic phase separation. 25g. aliquots of the stock solution were successively extracted with two 12g. portions of a 0.1 weight percent aqueous solution of the sequestering agent. Samples were heated to 50° C. to facilitate phase separation.

Table I below shows the iron initially present in the organic layer (A), the iron removed in the first aqueous extraction (B), the iron remaining with the organic layer after the first extraction (A-B), and the iron removed by the second aqueous extraction (C). The fraction of the available iron removed by each extraction is approximately constant. Rhodium material balances are also shown. Poor material balances were often seen in systems where emulsion problems were significant. The pH of each aqueous solution is also shown in the final column of Table I.

TABLE I
SEQUESTERING AGENTS FOR IRON

| | Iron Content of Initial and Extracted Solutions | | | | Fraction of Iron Extracted | | Rhodium Balance | | |
|---|---|---|---|---|---|---|---|---|---|
| | Initial mg. (A) | Removed by 1st Extn. mg. (B) | Remaining After 1st Extn. mg. (A-B) | Removed by 2nd Extn. mg. (C) | First Extraction % (B/A × 100) | Second Extraction % (C/A-B × 100) | Remaining in Organic Layer % | Aqueous/ Emulsion % | pH of Extracting Solution |
| Water | 3.60 | nil | 3.60 | 0.07 | 0 | 1.9 | 43 | 7 | 7 |
| EDTA[1] | 3.80 | 2.79 | 1.01 | 0.55 | 73.4 | 54.5 | 95 | nil | 4.7 |
| Oxalic Acid | 3.65 | 1.91 | 1.74 | 1.14 | 52.1 | 65.5 | 93 | nil | 1.6 |
| Tartaric Acid | 3.80 | 0.59 | 3.21 | 0.69 | 15.5 | 21.5 | 92 | nil | 2.3 |
| Sodium Pyrophosphate | 3.74 | 1.15 | 2.59 | 1.39 | 30.7 | 53.7 | 99 | nil | 10.1 |
| Sulfosalicylic Acid | 3.73 | 2.77 | 0.96 | 0.39 | 74.3 | 40.6 | 88 | nil | 1.8 |
| Glycine | 3.70 | nil | 3.70 | 0.14 | 0 | 3.8 | 44 | 4 | 6.6 |
| Diethylene | 3.66 | | 2.58 | 0.56 | 29.5 | 21.7 | 65 | 1 | 11.2 |
| Disodium nitrilotriacetate | 3.66 | 2.90 | 0.76 | 0.64 | 79.2 | 84.2 | 82 | nil | 3.4 |

[1] ethylenediamine tetracetic acid

EXAMPLE 2

The production rate of aldehyde condensation products in an operating Oxo plant for the rhodium catalyzed production of propionaldehyde was 27,000 lbs/day. The iron concentration in the catalyst solution was 366 ppm. Iron was extracted from the catalyst solution by adding an aqueous solution of disodio EDTA (65 lbs. in 1,500 gallons of water) to the reactor containing 3,500 gallons of catalyst solution. The mixture was agitated for 3-4 hours at a temperature of 70° C., forming a stable emulsion. The reactor contents were then transferred to a holding tank wherein 500 gallons of propionaldehyde were added and the mixture warmed to 50° C. to facilitate separation of the organic and aqueous layers. The bottom water layer was drawn off and the remaining organic layer returned to the reactor, the iron content of the organic layer having been reduced to 80 ppm. The production rate of aldehyde condensation products declined to 2,000 lbs/day.

What is claimed is:

1. In a process for producing aldehyde products by the rhodium catalyzed hydroformylation of alpha-olefins containing 2 to about 20 carbon atoms comprising: providing a liquid body of a homogeneous mixture containing olefin, aldehyde products and higher boiling aldehyde condensation products, a soluble rhodium catalyst complexed with carbon monoxide and triarylphosphine, at least 10 moles of free triarylphosphine being present for each mole of rhodium metal, the liquid body also containing iron salt contaminants which promote the formation of said condensation products; suppling to the liquid body a gaseous stream comprising hydrogen and carbon monoxide maintaining the temperature of the liquid body at 50° C. to about 130° C., the total pressure at less than about 400 psia, the improvement which comprises removing said iron salts from the liquid body by complexation with an aqueous solution of a sequestering agent, and thereafter removing the resulting iron complex in a separate aqueous phase.

2. The process of claim 1 wherein the gaseous recycle stream comprises hydrogen, the alpha-olefin and carbon monoxide.

3. The process of claim 1 wherein the triarylphosphine is triphenylphospine.

4. The process of claim 1 wherein the alpha-olefin is propylene.

5. The process of claim 1 wherein the olefin is ethylene.

6. The process of claim 1 wherein said chelating agent is a sequestering agent.

7. The process of claim 6 wherein said sequestering agent is an aminopolycarboxylic acid.

8. The process of claim 7 wherein said sequestering agent is ethylenediamine tetraacetic acid or a sodium salt thereof.

9. The process of claim 6 wherein said sequestering agent is a condensed phosphate.

10. The process of claim 9 wherein said sequestering agent is sodium pyrophosphate.

* * * * *

UNITED STATES PATENT AND TRADEMARK OFFICE
CERTIFICATE OF CORRECTION

PATENT NO. : 4,143,075
DATED : March 6, 1979
INVENTOR(S) : David R. Bryant

It is certified that error appears in the above–identified patent and that said Letters Patent are hereby corrected as shown below:

In TABLE I, bridging Columns 11 and 12, the eighth ingredient listed in column 1 of said TABLE I, shown as "Diethylene", should read ---Diethylene triamine---.

Signed and Sealed this

Ninth Day of October 1979

[SEAL]

Attest:

RUTH C. MASON
Attesting Officer

LUTRELLE F. PARKER
Acting Commissioner of Patents and Trademarks